United States Patent [19]
Hioki et al.

[11] Patent Number: 5,462,912
[45] Date of Patent: Oct. 31, 1995

[54] AGRICULTURAL CHEMICAL COMPOSITION ENHANCER COMPRISING QUATERNARY DI(POLYOXYALKYLENE) AMMONIUM ALKYL SULFATES

[75] Inventors: Yuichi Hioki; Kazuhiko Kurita; Keiko Kawabata; Toshikazu Azuma, all of Wakayama, Japan

[73] Assignee: Kao Corporation, Tokyo, Japan

[21] Appl. No.: 305,731

[22] Filed: Sep. 14, 1994

Related U.S. Application Data

[63] Continuation of Ser. No. 957,819, Oct. 8, 1992, abandoned.

[30] Foreign Application Priority Data

Oct. 9, 1991 [JP] Japan ................. 3-262014

[51] Int. Cl.$^6$ .................................................. A01N 25/30
[52] U.S. Cl. ................. 504/116; 504/206; 504/207; 504/300; 514/122; 514/132; 514/369; 514/493; 514/788; 514/975; 71/DIG. 1
[58] Field of Search .................. 504/206, 207, 504/330; 71/DIG. 1; 514/122, 132, 369, 493, 788, 975, 116

[56] References Cited

U.S. PATENT DOCUMENTS

| | | | |
|---|---|---|---|
| 3,979,307 | 9/1976 | Kolaian et al. | 252/8.75 |
| 4,118,324 | 10/1978 | Stekelberg et al. | 252/8.9 |
| 4,134,970 | 1/1979 | Panke et al. | 420/70 |
| 4,159,901 | 7/1979 | Beestman et al. | 504/206 |
| 4,540,521 | 10/1985 | Garst et al. | 260/459 A |
| 5,041,467 | 8/1991 | Kataoka et al. | 521/159 |

FOREIGN PATENT DOCUMENTS

| | | |
|---|---|---|
| 0274369 | 3/1987 | European Pat. Off. . |
| 2149329 | 6/1990 | Japan . |

OTHER PUBLICATIONS

Wyrill et al. "Glyphosate Toxicity . . . as Influenced by Surfactants". *Weed Science* 25:275–287. 1977.
11691 *Chemical Products.* The Chemical Daily Co., Ltd. p. 906 Jan. 23, 1991.

*Primary Examiner*—S. Mark Clardy
*Attorney, Agent, or Firm*—Birch, Stewart, Kolasch & Birch

[57] ABSTRACT

An agricultural chemical composition which can be safely applied to crops without causing any chemical damage; comprising a mixture, which exerts excellent potentiating effects on various agricultural chemicals, of compounds represented by the following general formula (I) and having (n1+n2+n3) and (n4+n5+n6) each being a number of 0 to 100 on the average, and an agricultural chemical, wherein the weight ratio of the mixture to the agricultural chemical ranges from 0.1 to 50:

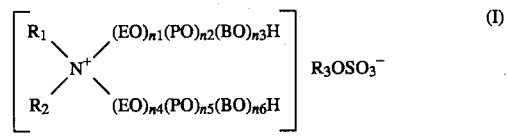

wherein $R_1$, $R_2$ and $R_3$ each represent a straight-chain or branched alkyl, alkenyl or hydroxyalkyl group having from 1 to 30 carbon atoms.

24 Claims, No Drawings

AGRICULTURAL CHEMICAL COMPOSITION ENHANCER COMPRISING QUATERNARY DI(POLYOXYALKYLENE) AMMONIUM ALKYL SULFATES

This application is a continuation, of application Ser. No. 07/957,819, filed on Oct. 8, 1992, now abandoned.

BACKGROUND OF THE INVENTION

1. Field of the Invention

The present invention relates to a novel agricultural chemical composition.

2. Description of the Related Art

Agricultural chemical compositions such as insecticide compositions, bactericide compositions, herbicide compositions, miticide compositions and plant growth regulator compositions have been used in various forms, for example, emulsions, wettable powders, granules, dusts or flowables. In the preparation of these agricultural chemical compositions, various attempts have been made to make good use of the efficacy of the agricultural chemical, but it has been found to be difficult under current circumstances to further potentiate the agricultural chemical through formulated contrivances. Further, it is difficult to develop various novel agricultural chemicals. Thus it is highly important from an industrial viewpoint to further potentiate the existing agricultural chemicals.

There have been known various surfactants which are nitrogen containing compounds (for example, quaternary ammonium salts, betaines and amine oxides) which can potentiate agricultural chemicals (refer to Japanese Patent Laid-Open No. 145205/1988). It is also known that quaternized ammonium salts comprising a long-chain alkyl group(s) and quaternized ammonium salts comprising a long-chain alkyl group(s) and a polyoxyethylene unit(s) are particularly effective therefor from among these surfactants. The above-mentioned quaternized ammonium salts capable of potentiating agricultural chemicals have halogen atoms as the counter ion. However the potentiating effects thereof are still unsatisfactory.

In 11691 *Chemical Products* (page 906, published on Jan. 23, 1991, ed. by The Chemical Daily Co., Ltd.) there was a quaternized di(hydroxyethylene) alkyl methyl ammonium methosulfate represented by the following formula (a):

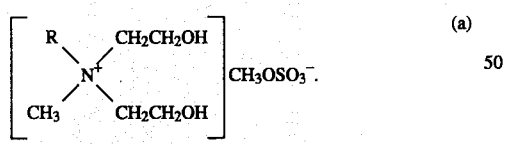

Japanese Patent Publication-A No. 149329/1990 (published on Jun. 7, 1990, NIPPON OILS & FATS K.K.) discloses a quaternized ammonium salt as an emulsifier for agricultural chemical compositions represented by the following formula (b):

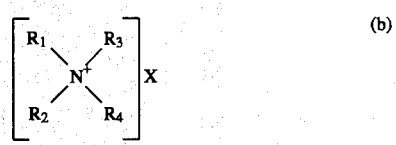

wherein $R_1$ and $R_2$ each represent an oleyl group, $R_3$ represents an alkyl group having 1 to 3 carbon atoms, $R_4$ represents an alkyl group having 1 to 3 carbon atoms or a poly (1 to 50) oxyethylene group and X represents a halogen atom, $-CH_3SO_4$ or $-C_2H_5SO_4$.

The above-described Japanese Patent Publication-A No. 149329/1990 (published on Jun. 7, 1990, NIPPON OILS & FATS K.K. ) further discloses a combination use of the above-described quaternized ammonium salt with a surfactant, e.g., a nonionic surfactant, a cationic surfactant and an amphoteric surfactant, other than the quaternized ammonium salt.

Furthermore, U.S. Pat. Nos. 4,118,324 and 4,134,970 (published on Oct. 3, 1978 and Jan. 16, 1979, HOECHST AG) discloses a quaternized ammonium salt for hair preparations and textile softeners represented by the following formula (c), U.S. Pat. No. 4,540,521 (published on Sep. 10, 1985, NATIONAL DISTILLERS CORP.) discloses a quaternized ammonium salt as an antistatic agent represented by the following formula (d), and U.S. Pat. No. 3,979,307 (published on Sep. 3, 1976, TEXACO INC.) discloses a quaternized ammonium salt as a fabric softener represented by the following formula (e):

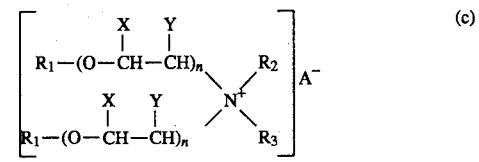

wherein $R_1$ represents an alkyl or alkenyl group having 8 to 24 carbon atoms, a cyclohexyl residue or an aryl group substituted by an alkyl group, $R_2$ and $R_3$ each represent an alkyl group having 1 to 4 carbon atoms or a benzyl group, X and Y each represent a hydrogen atom or a methyl group provided that X and Y are not methyl groups simultaneously, A represents a chlorine atom, a bromine atom, $-CH_3OSO_3$ or $-C_2H_5OSO_3$ and n is 1 to 20;

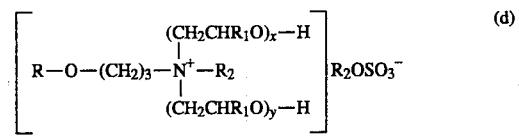

wherein R represents an aliphatic group having 5 to 19 carbon atoms, $R_1$ represents a hydrogen atom or a methyl group, $R_2$ represents an alkyl group having 1 to 4 carbon atoms, and X and Y are integers of 1 to 20; and

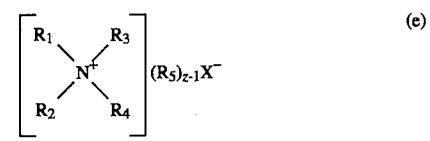

wherein $R_1$ and $R_2$ each represent sec. alkyl groups having 10 to 30 carbon atoms, $R_3$ represents a hydrogen atom, a methyl group or $(CH_2CH_2O)3H$, $R_4$ and $R_5$ each represent an alkyl group having 1 to 10 carbon atoms, an aryl group or an aralkyl group, X represents a sulfate or phosphate residue, and z is equal to the valency of X.

DISCLOSURE OF THE INVENTION

SUMMARY OF THE INVENTION

The present inventors have conducted extensive studies from the viewpoint that a combination of an agricultural chemical with a quaternary ammonium salt is effective in the potentiation of the agricultural chemical. As a result, they have found that a specific compound, which is selected from among quaternary ammonium salts, can exert a potentiating effect on various agricultural chemicals, thus completing the present invention.

Accordingly, the present invention provides an agricultural chemical composition (1) comprising or consisting essentially of a mixture of compounds represented by the following general formula (I), wherein (n1+n2+n3) and (n4+n5+n6) each are a number of 0 to 100 on the average, and an agricultural chemical, wherein the weight ratio of the mixture to the agricultural chemical ranges from 0.1 to 50:

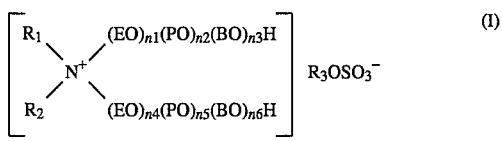

wherein $R_1$, $R_2$ and $R_3$ each represent a straight-chain or branched alkyl, alkenyl or hydroxyalkyl group having from 1 to 30 carbon atoms;

(EO)$_{n1}$ and (EO)$_{n4}$ each represent a polyoxyethylene chain;

(PO)$_{n2}$ and (PO)$_{n5}$ each represent a polyoxypropylene chain;

(BO)$_{n3}$ and (BO)$_{n6}$ each represent a polyoxybutylene chain;

n1, n2, n3, n4, n5 and n6 each are 0 or a positive integer; and (n1+n2+n3) and (n4+n5+n6) each are 0 or a positive integer provided that at least one of (n1+n2+n3) and (n4+n5+n6) is 1 or more.

The agricultural chemical means those materials which are employed as active ingredients for common agricultural chemical compositions, such as active ingredients of bactericides, insecticides, miticides, herbicides, plant growth regulators, etc., an agricultural medicine, a biocide, a matter being effective for an agricultural medicine or an agricultural medicine base.

The above-described present invention includes an agricultural chemical composition comprising an adjuvant comprising a compound represented by the following general formula (II) as an active ingredient and an agricultural chemical, wherein the weight ratio of the adjuvant to the agricultural chemical ranges from 0.1 to 50:

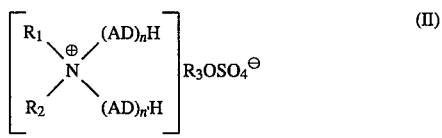

wherein $R_1$, $R_2$ and $R_3$ each represent a straight-chain or branched alkyl, alkenyl or hydroxyalkyl group having from 1 to 30 carbon atoms;

A is an alkylene group having from 2 to 4 carbon atoms; and n and n' each are a number of from 0 to 100, provided that n+n' is 1 or more.

The present invention also provides an agricultural chemical composition (2) comprising or consisting essentially of a mixture of compounds represented by the above general formula (I), wherein (n1+n2+n3) and (n4+n5+n6) each are a number of 0 to 100 on the average, and a surfactant other than said compounds as the adjuvants, and an agricultural chemical, wherein the weight ratio of the total amount of the adjuvants to the agricultural chemical ranges from 0.1 to 50.

The above-described present invention includes an agricultural chemical composition comprising an adjuvant comprising a compound represented by the above general formula (II) and a nonionic surfactant as the active ingredients and an agricultural chemical, wherein the weight ratio of the adjuvant to the agricultural chemical ranges from 0.1 to 50.

The present invention further provides a kit (1) comprising or consisting essentially of package (A) comprising or consisting essentially of a mixture of compounds represented by the above general formula (I), wherein (n1+n2+n3) and (n4+n5+n6) each are a number of 0 to 100 on the average, and package (B) comprising or consisting essentially of an agricultural chemical, wherein the weight ratio of the mixture to the agricultural chemical ranges from 0.1 to 50; a kit (2) comprising or consisting essentially of package (A) comprising or consisting essentially of a mixture of compounds represented by the above general formula (I), wherein (n1+n2+n3) and (n4+n5+n6) each are a number of 0 to 100 on the average, package (C) comprising or consisting essentially of a surfactant other than the compounds represented by the above general formula (I) and package (B) comprising or consisting essentially of an agricultural chemical, wherein the weight ratio of the total amount of the mixture and the surfactant to the agricultural chemical ranges from 0.1 to 50; and a kit (3) comprising or consisting essentially of package (D) comprising or consisting essentially of a mixture of compounds represented by the above general formula (I), wherein (n1+n2+n3) and (n4+n5+n6) each are a number of 0 to 100 on the average, and a surfactant other than the compounds represented by the above general formula (I) and package (B) comprising or consisting essentially of an agricultural chemical, wherein the weight ratio of the total amount of the mixture and the surfactant to the agricultural chemical ranges from 0.1 to 50.

The present invention provides a bactericidal, insecticidal, miticidal, herbicidal or plant growth regulating method (1) wherein an agricultural chemical composition (3) comprising from 0.02 to 8% by weight of a mixture of compounds represented by the above general formula (I), wherein (n1+n2+n3) and (n4+n5+n6) each are a number of 0 to 100 on the average, and an agricultural chemical which is present in an amount of from 0.02 to 10 times as much as the mixture, is employed, and a bactericidal, insecticidal, miticidal, herbicidal or plant growth regulating method (2) wherein an agricultural chemical composition (4) comprising from 0.02 to 8% by weight of adjuvants comprising or consisting essentially of a mixture of compounds represented by the above general formula (I), wherein (n1+n2+n3) and (n4+n5+n6) each are a number of 0 to 100 on the average, and a surfactant other than the compounds represented by the above general formula (I), and an agricultural chemical which is present in an amount of from 0.02 to 10 times as much as the total amount of the adjuvants, is employed.

Further scope and the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. Detailed Description of the Invention:

in the present invention, a mixture consisting essentially of compounds represented by the above-mentioned general formula (I) and having (n1+n2+n3) and (n4+n5+n6) each being a number of 0 to 100 on the average is used as an adjuvant. Namely, a mixture of compounds represented by the above general formula (I), which differ from each other at least one among n1, n2, n3, n4, n5 and n6, is employed. Certainly, a mixture comprising two or more of the above-described mixtures may be used as adjuvants.

In the above general formula (I), $R_1$, $R_2$ and $R_3$ each represent a straight-chain or branched alkyl, alkenyl or hydroxyalkyl group having from 1 to 30 carbon atoms.

In the compounds represented by the general formula (I) according to the present invention, it is preferable that $R_1$ represents a straight-chain or branched alkyl, alkenyl or hydroxyalkyl group having from 8 to 24 carbon atoms. Specific examples thereof include octyl, decyl, lauryl, myristyl, palmityl, stearyl and oleyl groups. When two or more of the mixtures are employed, it is recommended to use mixtures consisting essentially of compounds wherein $R_1$ represents a group selected from among those cited above. On the other hand, $R_2$ and $R_3$ may each preferably represent a straight-chain or branched alkyl, alkenyl or hydroxyalkyl group having from 1 to 4 carbon atoms. Specific examples thereof include methyl, ethyl, hydroxyethyl and hydroxypropyl groups.

The compound represented by the general formula (I) has at least one of a polyoxyethylene chain, a polyoxypropylene chain and a polyoxybutylene chain. That is, at least one of n1, n2, n3, n4, n5 and n6 is an integer of 1 or more.

When two or three kinds of alkylene oxide chains are present in the general formula (I), the addition of the alkylene oxide chains may be in block or at random.

The average of the numbers (n1+n4) of moles of the ethylene oxide added of the compounds constituting the mixture according to the present invention is taken as the number of moles of the ethylene oxide added of the mixture, the average of the numbers (n2+n5) of moles of the propylene oxide added of the compounds constituting the mixture is taken as the number of moles of the propylene oxide added of the mixture, and the average of the numbers (n3+n6) of moles of the butylene oxide added of the compounds constituting the mixture is taken as the number of moles Of the butylene oxide added of the mixture.

In the general formula (I), (n1+n2+n3) and (n4+n5+n6) are each 0 or a positive integer provided that at least one of (n1+n2+n3) and (n4+ n5+n6) is 1 or more.

The average of each the (n1+n2+n3)s and (n4+n5+n6)s of the compounds represented by the general formula (I), in other words, the (n1+n2+n3) of the mixture according to the present invention and the (n4+n5+n6) of the mixture according to the present invention is from 0 to 100, preferably from 0 to 50 and still preferably from 1 to 25. When these numbers exceed 100, the resulting compound has an excessively high molecular weight, which lowers the potentiating action per unit weight.

The (n1+n2+n3+n4+n5+n6) of the mixture according to the present invention is 1 or above, preferably from 1 to 100 and still preferably from 2 to 50.

Among the mixtures according to the present invention, quaternized N,N,N,N-lauryl ethyl di[(poly)oxyethylene] ($\overline{n1+n4}=2$) ammonium ethyl sulfate, which is a mixture of quaternized N,N,N,N-lauryl ethyl di[(poly)oxyethylene] ammonium ethyl sulfates differing from each other only in the number (n1+n4) of moles of the polyoxyethylene chain and which has an average number of moles the polyoxyethylene chains ($\overline{n1+n4}$) of 2, is particularly suitable in the present invention. Furthermore, quaternized N,N,N,N-oleyl methyl di[(poly)oxyethylene] ($\overline{n1+n4}=2$) ammonium methylsulfate, quaternized N,N,N,N-lauryl methyl di[(poly)oxyethylene] ($\overline{n1+n4}=15$) ammonium methylsulfate and quaternized N,N,N,N-oleyl methyl di[(poly)oxypropylene] ($\overline{n2+n5}=14$) ammonium methylsulfate are preferable.

The mixture consisting essentially of compounds represented by the general formula (I) according to the present invention may be produced by any commonly known method. For example, it may be obtained by adding dropwise a lower alkyl sulfate to a di(polyoxyalkylene)monoalkylamine at a high temperature (70° to 90° C.) followed by aging. The alkyl group of the di(polyoxyalkylene)monoalkylamine to be used as the starting material in this reaction is a straight-chain or branched alkyl group having from 1 to 30 carbon atoms. Alternately, an amine having an alkenyl group, which has a double bond in the chain, or a hydroxyalkyl group, which has a hydroxyl group in the chain, instead of the alkyl group may be used. It is preferable that the starting amine has a hydrocarbon group, such as an alkyl group, having from 8 to 24 carbon atoms. It is still preferable that the starting amine has a hydrocarbon group having from 8 to 24 carbon atoms and from 0 to 4 (still more preferably from 0 to 2) double bonds and/or from 0 to 4 (still more preferably from 0 to 2) hydroxyl groups.

When used together with an agricultural chemical, the mixture consisting essentially of the compounds represented by the above general formula (I) as an adjuvant can enhance the effects of the agricultural chemical twice or thrice without causing any chemical damage.

It is not necessarily evident why the mixture comprising compounds represented by the above general formula (I) according to the present invention has the remarkable effect of potentiating any agricultural chemicals irrespective of its structure. It is conceivable, however, that one reason therefor may reside in the fact that the mixture according to the present invention has such a potent power of solubilizing the agricultural chemical that the agricultural chemical becomes finely grained, thus promoting the diffusion of the agricultural chemical on a surface of a plant, an insect or a bacterial cell thus facilitating the permeation of the agricultural chemical into the plant, insect or bacterial cell.

When the mixture comprising compounds represented by the general formula (I) according to the present invention is used together with a surfactant other than the compounds represented by the general formula (I), the amount of the mixture can be reduced and the stability of an agricultural chemical composition can be increased while the potentiating effect of the mixture on agricultural chemicals is maintained. Examples of the surfactant usable herein include nonionic, anionic, cationic and amphoteric surfactants, and mixtures thereof.

Examples of the nonionic surfactants include polyoxyethylene alkyl ethers, polyoxyethylene alkylaryl ethers, polyoxyethylene alkylaryl ether/formaldehyde condensates, polyoxyalkylene aryl ethers, polyoxyalkylene alkyl esters, polyoxyalkylene alkyl sorbitol esters, polyoxyalkylene sorbitan esters, polyoxyalkylene alkyl glycerol esters, polyoxyalkylene block copolymers, polyoxyalkylene block copolymer alkylglycerol esters, polyoxyalkylene alkyl sulfonamides, polyoxyalkylene rosin esters, polyoxypropylene block copolymers, polyoxyethylene oleyl ethers, polyoxyalkylene alkylphenols and mixtures consisting of two or more of these substances.

Examples of the cationic surfactants include polyoxyalkylaminos such as ethoxylated tallow amine, ethoxylated oleylamine, ethoxylated soy amine, ethoxylated coco amine, ethoxylated synthetic alkylamine and ethoxylated octylamine and mixtures consisting of two or more of these substances.

Examples of the anionic surfactants, which are typically available in the form of an aqueous solution or a solid, include sodium aryl sulfate, sodium mono- or di-alkylnapthalenesulfonates, sodium α-oleinsulfonate, sodium alkanesulfonate, alkyl sulfates, polyoxyalkylene alkyl ether sulfonates, polyoxyalkylene alkylaryl ether sulfates, polyoxyalkylene styrylphenyl ether sulfates, mono- or di-alkylbenzenesulfonates, alkylnapthalenesulfonates, alkylnaphthalenesulfonate/formaldehyde condensates, alkyl diphenyl ether sulfonates, olefinic sulfonates. alkyl phosphates, polyoxyalkylene alkyl phosphates, polyoxyalkylene phenyl ether phosphates, polyoxyalkylphenol phosphates, polycarboxylic acid salts, fatty acid salts, stearic acid and its salts, oleic acid and its salts, N-methyl fatty acid taurides and mixtures consisting of two or more compounds selected from among those cited above, involving sodium, potassium, ammonium and amine salts.

Examples of suitable amphoteric surfactants include lauryldimethylamine oxide, Armox C mfd. by Lion Co., Ltd., Carinal mfd. by Toho Chemical Co., Ltd., Amphitol 24B mfd. by Kao Corporation, betaines, other amine oxides and mixtures consisting of two or more substances selected from among those cited above.

Among these surfactants, nonionic surfactants are particularly preferable. It is still preferable to use ester-type surfactants such as polyoxyalkylene sorbitan esters and polyoxyalkylene alkyl glycerol esters; polyoxyalkylene alkyl ethers and polyoxyalkylene alkylnonylphenols.

Although the ratio of the mixture comprising compounds represented by the general formula (I) to the surfactant other than the compounds represented by the general formula (I) in the agricultural chemical composition (2) is not particularly restricted, the weight ratio of the mixture comprising compounds represented by the general formula (I) to the surfactant other than the above-described compounds may range from 1/10 to 50/1, preferably from 1/1 to 10/1.

The agricultural chemical composition (1) of the present invention comprises the mixture comprising compounds represented by the general formula (I) as an adjuvant and an agricultural chemical. It is necessary for the agricultural chemical composition (1) of the present invention to have a weight ratio of the adjuvant to the agricultural chemical within a range of from 0.1 to 50, preferably from 0.1 to 10. When this weight ratio is below 0.1, no satisfactory effect can be achieved. When this ratio exceeds 50, on the other hand, the effect cannot be further improved.

The agricultural chemical composition (2) of the present invention comprises the mixture comprising compounds represented by the general formula (I) and the surfactant other than the compounds represented by the general formula (I) as the adjuvants and an agricultural chemical. It is necessary for the agricultural chemical composition (2) of the present invention to have a weight ratio of the total amount of the adjuvants to the agricultural chemical within a range of from 0.1 to 50, preferably from 0.1 to 10. When this weight ratio is below 0.1, no satisfactory effect can be achieved. When this ratio exceeds 50, on the other hand, the effect cannot be further improved.

The agricultural adjuvant(s) according to the present invention can be safely applied to various crops without causing any chemical damage.

The agricultural chemical compositions (1) and (2) of the present invention may be in any preparation form, for example, an emulsion, a wettable powder, granules, a flowable powder or dusts, without restriction. Thus, the agricultural chemical compositions (1) and (2) according to the present invention may further contain other additives such as emulsifiers, dispersing agents and supports depending on the preparation form.

Now, agricultural chemicals and agricultural chemical compositions (i.e., agricultural chemical formulations) which can be used in the preparation of the agricultural chemical compositions (1) and (2) of the present invention will be described, though it is to be understood that the present invention is not restricted thereto.

In the case of bactericides, namely, in the case that the agricultural chemical compositions (1) or (2) is a bactericide composition, agricultural chemicals or agricultural chemical compositions used in the present invention include Dipher (zinc ethylenebisdithiocarbamate) mfd. by Sankyo Co., Ltd., Manebdithane (manganese ethylenebisdlthiocarbamate) mfd. by Sankyo Co., Ltd., Thiuram 80 [bls(dimethylthiocarbamoyl) disulfide] mfd. by Sankyo Co., Ltd., Manzeb (zinc/manganese ethylenebisdithlocarbamate) mfd. by Tokyo Organic Chemical Industries Co., Ltd., Bisdithane (bisdimethyldithiocarbamoyl zinc ethylenebisdithiocarbamate) mfd. by Sankyo Co., Ltd., Antracol (zinc propylenebisdithiocarbamate) mfd. by Nihon Bayer Agrochem K.K., benzimidazole bactericides such as Benlate [methyl 1-(butylcarbamoyl)-2-benzimidazolecarbamate] mfd. by Sankyo Co., Ltd. and Thopsin M [1,2-bis(3-methoxycarbonyl-2-thioureido)benzene] mfd. by Nippon Soda K.K., Ronilan [3-(3,5-dichlorophenyl)- 5-methyl-5-vinyl-l,3-oxazolidine-2,4-dione] mfd. by Sankyo Co., Ltd., Rovral [3-(3,5-dichlorophenyl)-N-isopropyl- 2,4-dioxoimidazolidine-1-carboxamide] mfd. by Shionogi Pharmaceutical Co., Ltd., Sumilex [N-(3,5-dichlorophenyl)- 1,2-dimethylcyclopropane-1,2-dicarboximide] mfd. by Sumitomo Chemical Co., Ltd., Triazine [2,4-dichloro-6-(2-chloroanilino)-1,3,5-triazine] mfd. by Nippon Soda K.K., Trifmine [(E)-4-chloro-α,α,α-trifluoro-N-(1-imidazol-1-yl-2-propoxyethylidene-o-toluidine] mfd. by Nippon Soda K.K., Ridomil [methyl N-(2-methoxyacetyl)-N-( 2,6-xylyl)-D,L-alaninate] mfd. by Sankyo Co., Ltd., Baycoral [all-rac-1-(biphenyl-4-yloxy)-3,3-dimethyl-1-( 1H-1,2,4-triazol-1-yl)-2-butan-2-ol] mfd. by Nihon Bayer Agrochem K.K., Bayleton [1-(4-chlorophenoxy)- 3,3-dimethyl-1-(1,2,4-triazol-1-yl)-2-butanone] mfd. by Nihon Bayer Agrochem K.K., Fuji-One (diisopropyl 1,3-dithiolan-2-ylidenemalonate) mfd. by Nihon Nouyaku K.K., Daconil (tetrachloroisophthalonitrile) mfd. by Kumiai Chemical K.K., Pansoil (5-ethoxy-3-trichloromethyl- 1,2,4-thiadiazole) mfd. by Sankyo Co., Ltd., Rabcide (4,5,6,7-tetrachlorophthalide) mfd. by Sankyo Co., Ltd., Kitazin P (O,O-diisopropyl-S-benzyl thiophosphate) mfd. by Kumiai Chemical K.K., Hinosan (O-ethyl-S,S-diphenyl dithiophosphate) mfd. by Sankyo Co., Ltd., Oryzemate (3-allyloxy-1, 2-benzisothiazole 1,1-dioxide) mfd. by Meiji Seika Co., Ltd. and Orthocide (N-trichloromethylthio-tetrahydrophthalimide) mfd. by Sankyo Co., Ltd.

In the case of insecticides, they include pyrethroid insecticides such as Fenvalerate [α-cyano- 3-phenoxybenzyl-2-(4-chlorophenyl)-3-methylbutanoate], e.g., Vegiphon mfd. by Sankyo Co., Ltd., and Baytroid [cyano-4-fluoro-3-phenoxyphenylmethyl 3-(2,2-dichloroethenyl)- 2,2-dimethylcyclopropanecarboxylate] mfd. by Nihon Bayer Agrochem K.K., organophosphorus insecticides such as DDVP (2,2-dichlorovinyl dimethyl phosphate), e.g., Des mfd. by Sankyo Co., Ltd., Sumithion (0,0-dimethyl-O-(3-methyl-4-nitrophenyl)thiophosphate) mfd. by Sumitomo Chemical Co.; Ltd., Malathion (S-[1,2-bis(ethoxycarbonyl)ethyl]dimethyl phosphorothiolthionate) mfd. by Sankyo Co., Ltd., Dimethoate [dimethyl S-(N-methylcarbamoylmethyl) dithiophosphate] mfd. by Sankyo Co., Ltd., Papthion (S-[α-(ethoxycarbonyl)benzyl]dimethyl phosphorothiolthionate)

mfd. by Sankyo Co., Ltd., and Baycid [O,O-dimethyl O-(3-methyl-4-methylthiophenyl)thiophosphate], carbamate insecticides such as Bassa (o-butylphenyl methylcarbamate) mfd. by Sankyo Co., Ltd., Tsumacide (m-tolyl methylcarbamate) mfd. by Sankyo Co., Ltd., Meobal (3,4-dimethylphenyl N-methylcarbamate) mfd. by Sankyo Co., Ltd., and Papnac (1-naphthyl N-methylcarbamate) mfd. by Sankyo Co., Ltd., and Lannate (S-methyl-N-[(methylcarbamoyl)oxy]thioacetoimide) mfd. by Sankyo Co., Ltd., and Padan [1,3-bis(carbamoylthio)-2-(N,N-dimethylamino)propane hydrochloride] mfd. by Takeda K.K.

In the case of miticides, they include Acricid (2,4-dinitro-6-sec-butylphenyl dimethylacrylate) mfd. by Sankyo Co., Ltd., Akar (ethyl 4,4-dichlorobenzilate) mfd. by Sankyo Co., Ltd., Kelthane [1,1-bis(p-chlorophenyl)- 2,2,2-trichloroethanol] mfd. by Sankyo Co., Ltd., Omite [2-(p-tert-butylphenoxy)cyclohexyl 2-propinyl sulfite] mfd. by Uniroyal Chemical Co., Ltd., Osadan [hexakis($\beta,\beta$-dimethylphenethyl)distannoxane] mfd. by Shell Chemical Co., Ltd., Nissorun [trans-5-(4-chlorophenyl)-N-cyclohexyl- 4-methyl-2-oxothiazolldine-3-carboxamide] mfd. by Nippon Soda K.K., and Dani-Cut [3-methyl-l,5-bis(2,4-xylyl)- 1,3,5-triazapenta-1,4-diene] mfd. by Nissan Chemical Co., Ltd.

In the case of herbicides, they include Stam (3,4-dichloropropionanilide) mfd. by Sankyo Co., Ltd, Saturn [S-(4-chlorobenzyl) N,N-diethylthiolcarbamate] mfd. by Kumiai Chemical K.K., Roundup [N-(phosphonomethyl)glycine isorpopylamine salt] mfd. by Monsant, Karmex [3-(3,4-dichlorophenyl)-1,1-dimethylurea] mfd. by Tomono Agrichemical K.K., Paraquat (1,1-dimethyl- 4,4'-dipyridinium dichloride) mfd. by Nihon Agrichemical K.K., Basra [ammonium DL-homoalanin-4-yl(methyl)phosphinate] mfd. by Ishihara K.K., Herbace (sodium salt of L-2-amino-4-[(hydroxy)(methyl)phosphinoyl] butylyl-L-alanyl-L-alanine) mfd. by Meiji Seika Co. Ltd.

In the case of plant growth regulators, they include MH (maleic hydrazide), Ethrel (2-chloroethylphosphonic acid), UASTA and Bialaphos.

The agricultural chemical compositions (1) and (2) of the present invention may further contain one or more plant growth regulators other than those cited above, fertilizers and preservatives.

The agricultural chemical compositions (1) and (2) according to the present invention may contain all components and it may be used as it is or after dilution. Alternately, the agricultural chemical compositions (1) and (2) may be prepared before using by blending or mixing an agricultural chemical composition free from the above-described adjuvant(s) with the above-described adjuvant(s), and it may be used as it is or after dilution. The potentiating effect due to the above-described adjuvant(s) according to the present invention can be achieved in either case.

The kit (1) according to the present invention which comprises package (A) comprising a mixture of compounds represented by the above general formula (I) and having (n1+n2+n3) and (n4+n5+n6) each being a number of 0 to 100 on the average and package (B) comprising an agricultural chemical is used for the preparation of the agricultural chemical composition (1).

The kit (2) according to the present invention which comprises package (A) comprising a mixture of compounds represented by the above general formula (I) and having (n1+n2+n3) and (n4+n5+n6) each being a number of 0 to 100 on the average, package (C) comprising a surfactant other than the compounds represented by the above general formula (I) and package (B) comprising an agricultural chemical, and the kit (3) according to the present invention which comprises package (D) comprising a mixture of compounds represented by the above general formula (I) and having (n1+n2+n3) and (n4+n5+n6) each being a number of 0 to 100 on the average and a surfactant other than the compounds represented by the above general formula (I) and package (B) comprising an agricultural chemical, are used for the preparation of the agricultural chemical composition (2).

For package (B), a package comprising a commercially available agricultural chemical composition, that is, an agricultural chemical formulation, may be employed. The commercially available agricultural chemical composition may be a preparation form of an emulsion, a solution, a wettable powder, a granule, a flowable powder or a dust.

In the present invention, agricultural chemical compositions (3) and (4), each of which contains from 0.02 to 8% by weight of the adjuvant(s) according to the present invention and an agricultural chemical 0.02 to 10 times as much as the adjuvant(s), are used in order to achieve the bactericidal, insecticidal, miticidal, herbicidal or plant growth regulating effects. The agricultural chemical compositions (3) and (4) are generally prepared by diluting the agricultural chemical compositions (1) and (2), respectively.

EXAMPLES

To further illustrate the present invention in greater detail, and not by way of limitation, the following Examples are given.

PRODUCTION EXAMPLE 1

221.0 g of dioxyethylene laurylamlne (total mole number of oxyethylenes=2) was fed into a four-necked flask and dehydrated at 90° C. under reduced pressure (160 mmHg) for 30 minutes, followed by the adjusting of the pressure to the atmospheric level. Then it was cooled to 70° to 80° C. and 119.1 g of diethyl sulfate, equimolar with the dioxyethylene laurylamine, was slowly added into the flask dropwise while stirring. After aging under stirring for 5 hours, a quaternized product of dioxyethylene laurylamine with diethyl sulfate, i.e., quaternized N,N,N,N-lauryl ethyl di[ (poly)oxyethylene] ($\overline{n1+n4}$ in formula (I)=2) ammonium ethyl sulfate, was obtained (adjuvant 1). The conversion rate was 99.1%.

EXAMPLE 1

The product obtained in the above Production Example 1 was dissolved in deionized water to give a 0.2% by weight solution thereof. The marketed herbicides, namely Roundup solution (active ingredient: 41% by weight), Karmex wettable powder (active ingredient: 78.5% by weight) and Herbiace water-soluble powder (active ingredient: 20% by weight) were each diluted 300-fold with the obtained 0.2% solution. Thus three agricultural chemical compositions of the present invention were obtained.

Then 10 ml/pot of each of the above-mentioned agricultural chemical compositions was applied onto crabgrass (a woody herb), which had been uniformly grown, to thereby evaluate the herbicidal effect.

The herbicidal rate (%) was expressed in the ratio of the fresh weight of the above-ground part measured 10 days after the application to that of the control (untreated) lot [refer to formula (III)].

$$\text{herbicidal effect} = \frac{\text{(above-ground part fresh weight of control lot)} - \text{(above-ground part fresh weight of test lot)}}{\text{(above-ground part fresh weight of control lot)}} \times \frac{100}{(\%)}$$

The above procedure was repeated except that the agricultural adjuvant 1 was replaced with each of the following agricultural adjuvants 2 to 22. Thus the herbicidal effect of each agricultural chemical composition was evaluated. Further, the herbicidal effects of the dilutions of the above marketed agricultural chemical compositions alone (free from any potentiator) were also evaluated in the same manner. Tables 1A and 1B summarize the results.

Adjuvant 2:
  Adjuvant 1/Emulgen 909 [POE(9) nonylphenol ether, mfd. by Kao Corporation]=80/20.
Adjuvant 3:
  Adjuvant 1/Emulgen 103 [POE(3) $C_{12}H_{25}OH$, mfd. by Kao Corporation]=80/20.
Adjuvant 4:
  Adjuvant 1/Emunon 4110 [POE(10) $C_{17}H_{35}COOH$, mfd. by Kao Corporation]=80/20.
Adjuvant 5:
  Adjuvant 1/Rheodol TWL-120 [sorbitan ester of POE(20) $C_{11}H_{23}COOH$, mfd. by Kao Corporation]=80/20.
Adjuvant 6:
  quaternized N,N,N,N-oleyl methyl di[(poly)oxyethylene] ($\overline{n1+n4}$ in formula (I)=2) ammonium methylsulfate.
Adjuvant 7:
  Adjuvant 6/Emulgen 703 [POE(3) $C_{12}H_{25}OH$/POE(3) $C_{13}H_{27}OH$ mixture, mfd. by Kao Corporation]=75/25.
Adjuvant 8:
  Adjuvant 6/Emanon 1112 [POE(12) $C_{11}H_{23}COOH$, mfd. by Kao Corporation]=75/25.
Adjuvant 9:
  Adjuvant 6/Rheodol TWO-120 [sorbitan ester of POE(20) $C_{17}H_{33}COOH$, mfd. by Kao Corporation]=75/25.
Adjuvant 10:
  didecyldimethylammonium chloride.
Adjuvant 11:
  monolauryltrimethylammonium chloride.
Adjuvant 12:
  dilauryldihydroxyethylammonium chloride.
Adjuvant 13:
  trimethylcocoammonium chloride.
Adjuvant 14:
  quaternized N,N,N,N-lauryl methyl di[(poly)oxyethylene]($\overline{n1+n4}$ in formula (I)=15) ammonium methylsulfate.
Adjuvant 15:
  Adjuvant 14/Emulgen 909=80/20.
Adjuvant 16:
  Adjuvant 14/Emulgen 103=80/20.
Adjuvant 17:
  Adjuvant 14/Emunon 4110=80/20.
Adjuvant 18:
  Adjuvant 14/Rheodol TWL-120=80/20.
Adjuvant 19:
  quaternized N,N,N,N-oleyl methyl di[(poly)oxypropylene]($\overline{n2+n5}$ in formula (I)=14) ammonium methylsulfate.
Adjuvant 20:
  Adjuvant 19/Emulgen 703=75/25.
Adjuvant 21:
  Adjuvant 19/Emunon 1112=75/25.
Adjuvant 22:
  Adjuvant 19/Rheodol TWO-120=75/25.

Note:
POE means polyoxyethylene. The compounds having POE are provided as mixtures and each number in the parentheses shows the average of the total number of moles of oxyethylene in the molecule. When two compounds are used together (adjuvants 2 to 5, 7 to 9, 15 to 18 and 20 to 22), the ratio given above is by weight.

TABLE 1A

| | Adjuvant (No.) | Herbicidal rate (%) | | |
|---|---|---|---|---|
| | | Karmex wettable powder | Herbiace water-soluble powder | Roundup solution |
| Invention composition | 1 | 98.5 | 99.3 | 100.0 |
| | 2 | 99.3 | 100.0 | 100.0 |
| | 3 | 100.0 | 100.0 | 100.0 |
| | 4 | 100.0 | 100.0 | 99.0 |
| | 5 | 100.0 | 100.0 | 100.0 |
| | 6 | 98.9 | 100.0 | 98.7 |
| | 7 | 100.0 | 99.3 | 99.3 |
| | 8 | 100.0 | 99.5 | 100.0 |
| | 9 | 100.0 | 100.0 | 100.0 |
| Comparative composition | 10 | 63.5 | 70.0 | 69.5 |
| | 11 | 44.5 | 72.2 | 70.0 |
| | 12 | 60.3 | 70.1 | 71.1 |
| | 13 | 50.3 | 67.8 | 70.5 |
| No adjuvant added | | 18.4 | 67.5 | 68.5 |

TABLE 1B

| | Adjuvant (No.) | Herbicidal rate (%) | | |
|---|---|---|---|---|
| | | Karmex wettable powder | Herbiace water-soluble powder | Roundup solution |
| Invention composition | 14 | 99.3 | 99.0 | 99.0 |
| | 15 | 98.9 | 100.0 | 100.0 |
| | 16 | 99.3 | 100.0 | 100.0 |
| | 17 | 98.9 | 98.1 | 100.0 |
| | 18 | 100.0 | 99.0 | 100.0 |
| | 19 | 98.9 | 100.0 | 99.3 |
| | 20 | 100.0 | 98.9 | 99.3 |
| | 21 | 100.0 | 99.0 | 99.3 |
| | 22 | 100.0 | 100.0 | 100.0 |
| No adjuvant added | | 18.4 | 67.5 | 68.5 |

EXAMPLE 2

Female *Tetranychus kanzawai* imagines were transplanted onto a kidney bean leaf disc (each lot having 30 insects, three runs) and incubated at 25° C. for 24 hours. Then the whole leaf disc was immersed in a test solution for 5 seconds. After allowing to stand at 25° C. for 48 hours, the disc was observed to determine the insecticidal rate based on the control lot (refer to the method employed for determining the herbicidal rates). As miticides, Nissolan V emulsion (active ingredient: 55% by weight) and Osadan wettable powder (active ingredient: 15% by weight), each diluted 2,000-fold, were used. The same adjuvants as those employed in the above Example 1 were used. These adjuvants were added to each of the diluted solutions in such a manner as to give a concentration of 0.1% by weight. In the case where no adjuvant was added to each of the diluted solutions (free from any potentiator), the same procedure was conducted. Tables 2A and 2B show the results.

TABLE 2A

| | Adjuvant (No.) | Miticidal rate (%) | |
|---|---|---|---|
| | | Nissolan V emusion | Osadan wettable powder |
| Invention composition | 1 | 99.4 | 100.0 |
| | 2 | 100.0 | 100.0 |
| | 3 | 100.0 | 100.0 |
| | 4 | 100.0 | 100.0 |
| | 5 | 100.0 | 100.0 |
| | 6 | 100.0 | 100.0 |
| | 7 | 100.0 | 98.8 |
| | 8 | 100.0 | 99.2 |
| | 9 | 100.0 | 100.0 |
| Comparative composition | 10 | 50.0 | 55.0 |
| | 11 | 50.0 | 54.0 |
| | 12 | 49.8 | 60.0 |
| | 13 | 50.0 | 58.8 |
| No adjuvant added | | 48.8 | 52.3 |

TABLE 2B

| | Adjuvant (No.) | Miticidal rate (%) | |
|---|---|---|---|
| | | Nissolan V emusion | Osadan wettable powder |
| Invention composition | 14 | 97.8 | 100.0 |
| | 15 | 97.8 | 100.0 |
| | 16 | 94.4 | 100.0 |
| | 17 | 94.4 | 100.0 |
| | 18 | 100.0 | 94.4 |
| | 19 | 100.0 | 94.4 |
| | 20 | 100.0 | 97.8 |
| | 21 | 100.0 | 94.4 |
| | 22 | 100.0 | 100.0 |
| No adjuvant added | | 48.8 | 52.3 |

EXAMPLE 3

Rice insect larvae of the third instar were incubated to evaluate the effect of each insecticide by the dipping method (three runs, each lot having 10 larvae). The insecticidal rate was determined in the same manner as the one used above for determining the miticidal rates. Each of the same adjuvants as those employed in the above Example 1 was dissolved in the marketed insecticides, namely, Sumithion emulsion (active ingredient: 50% by weight) or Malathion emulsion (active ingredient: 50% by weight), each diluted 2,000-fold, in such a manner as to give a concentration of 0.14 by weight. Tables 3A and 3B summarize the results.

TABLE 3

| | Adjuvant (No.) | Insecticidal rate (%) | |
|---|---|---|---|
| | | Sumithion emulsion | Malathion emulsion |
| Invention composition | 1 | 88.2 | 90.3 |
| | 2 | 100.0 | 100.0 |
| | 3 | 85.4 | 76.4 |
| | 4 | 80.2 | 90.4 |

TABLE 3-continued

| | Adjuvant (No.) | Insecticidal rate (%) | |
|---|---|---|---|
| | | Sumithion emulsion | Malathion emulsion |
| | 5 | 100.0 | 100.0 |
| | 6 | 92.3 | 98.2 |
| | 7 | 100.0 | 100.0 |
| | 8 | 90.4 | 96.6 |
| | 9 | 100.0 | 99.2 |
| Comparative composition | 10 | 59.2 | 45.5 |
| | 11 | 52.4 | 47.4 |
| | 12 | 58.6 | 44.6 |
| | 13 | 58.4 | 43.5 |
| No adjuvant added | | 52.4 | 43.2 |

TABLE 3B

| | Adjuvant (No.) | Insecticidal rate (%) | |
|---|---|---|---|
| | | Sumithion emulsion | Malathion emulsion |
| Invention composition | 14 | 86.7 | 90.0 |
| | 15 | 100.0 | 100.0 |
| | 16 | 86.7 | 90.0 |
| | 17 | 88.0 | 90.0 |
| | 18 | 100.0 | 100.0 |
| | 19 | 88.0 | 96.7 |
| | 20 | 100.0 | 100.0 |
| | 21 | 84.0 | 96.7 |
| | 22 | 100.0 | 96.7 |
| No adjuvant added | | 52.4 | 43.2 |

The above Examples 1, 2 and 3 show the effects of the adjuvants according to the present invention through the comparison compositions containing the adjuvant(s) according to the present invention with compositions containing common cationic surfactants as an adjuvant. As Tables 1A, 1B, 2A, 2B, 3A and 3B clearly indicate, the adjuvants according to the present invention remarkably potentiated agricultural chemicals and their effects were a practically usable level. On the other hand, the common cationic surfactants somewhat potentiated agricultural chemicals but their effects were far from a practically usable level. It is, therefore, understandable that the adjuvants according to the present invention remarkably potentiate agricultural chemicals, compared with common cationic surfactants. In particular, the combination use of the mixture comprising compounds represented by the general formula (I) with an ester-type nonionic surfactant showed excellent potentiating effects to agricultural chemicals.

EXAMPLE 4

The test described in the above Example 1 was repeated except that Roundup solution and the adjuvants 1 or 14 described in Example 1 were employed, each in the amount specified in Tables 4A (the adjuvant 1 was used) and 4B (the adjuvant 14 was used), respectively as a herbicide and as an adjuvant. Tables 4A and 4B show the results.

TABLE 4A

| Test No. | Content of Agricultural chemical (ppm) | Content of Adjuvant (ppm) | Agr. chemical/ Adjuvant (weight ratio) | Herbicidal rate (%) |
|---|---|---|---|---|
| 1 | 2000 | 200 | 1/0.1 | 85.1 |

TABLE 4A-continued

| Test No. | Content of Agricultural chemical (ppm) | Content of Adjuvant (ppm) | Agr. chemical/ Adjuvant (weight ratio) | Herbicidal rate (%) |
| --- | --- | --- | --- | --- |
| 2 | 2000 | 1000 | 1/0.5 | 98.5 |
| 3 | 2000 | 2000 | 1/1.0 | 99.0 |
| 4 | 2000 | 10000 | 1/5 | 99.4 |
| 5 | 2000 | 24000 | 1/12 | 100.0 |
| 6 | 2000 | 30000 | 1/15 | 100.0 |
| 7 | 2000 | 60000 | 1/30 | 100.0 |
| 8 | 2000 | 0 | — | 30.4 |
| 9 | 0 | 0 | — | 0.0 |

TABLE 4B

| Test No. | Content of Agricultural chemical (ppm) | Content of Adjuvant (ppm) | Agricultural chemical/ Adjuvant (weight ratio) | Herbicidal rate (%) |
| --- | --- | --- | --- | --- |
| 10 | 2000 | 200 | 1/0.1 | 69.0 |
| 11 | 2000 | 1000 | 1/0.5 | 80.0 |
| 12 | 2000 | 2000 | 1/1.0 | 99.0 |
| 13 | 2000 | 10000 | 1/5 | 100.0 |
| 14 | 2000 | 24000 | 1/12 | 100.0 |
| 15 | 2000 | 30000 | 1/15 | 100.0 |
| 16 | 2000 | 60000 | 1/30 | 100.0 |
| 17 | 2000 | 0 | — | 30.4 |
| 18 | 0 | 0 | — | 0.0 |

EXAMPLE 5

The test described in the above Example 1 was repeated except that Roundup solution and the adjuvants 6 or 19 described in Example 1 were employed, each in the amount specified in Tables 5A (the adjuvant 6 was used) and 5B (the adjuvant 19 was used), respectively as a herbicide and as an adjuvant. Tables 5A and 5B show the results.

TABLE 5A

| Test No. | Content of Agricultural chemical (ppm) | Content of Adjuvant (ppm) | Agr. chemical/ Adjuvant (weight ratio) | Herbicidal rate (%) |
| --- | --- | --- | --- | --- |
| 1 | 2000 | 200 | 1/0.1 | 88.1 |
| 2 | 2000 | 1000 | 1/0.5 | 97.5 |
| 3 | 2000 | 2000 | 1/1.0 | 98.2 |
| 4 | 2000 | 10000 | 1/5 | 96.6 |
| 5 | 2000 | 24000 | 1/12.0 | 95.5 |
| 6 | 2000 | 60000 | 1/30 | 100.0 |
| 7 | 2000 | 80000 | 1/40 | 100.0 |
| 8 | 2000 | 0 | — | 30.4 |
| 9 | 0 | 0 | — | 0.0 |

TABLE 5B

| Test No. | Content of Agricultural chemical (ppm) | Content of Adjuvant (ppm) | Agr. chemical/ Adjuvant (weight ratio) | Herbicidal rate (%) |
| --- | --- | --- | --- | --- |
| 10 | 2000 | 200 | 1/0.1 | 68.2 |
| 11 | 2000 | 1000 | 1/0.5 | 79.1 |
| 12 | 2000 | 2000 | 1/1.0 | 98.3 |
| 13 | 2000 | 10000 | 1/5 | 100.0 |
| 14 | 2000 | 24000 | 1/12.0 | 100.0 |
| 15 | 2000 | 60000 | 1/30 | 100.0 |
| 16 | 2000 | 80000 | 1/40 | 100.0 |
| 17 | 2000 | 0 | — | 30.4 |

TABLE 5B-continued

| Test No. | Content of Agricultural chemical (ppm) | Content of Adjuvant (ppm) | Agr. chemical/ Adjuvant (weight ratio) | Herbicidal rate (%) |
| --- | --- | --- | --- | --- |
| 18 | 0 | 0 | — | 0.0 |

EXAMPLE 6

The test described in the above Example 1 was repeated except that Roundup solution and the adjuvants 2 or 15 described in Example 1 were employed, each in the amount specified in Tables 6A (the adjuvant 2 was used) and 6B (the adjuvant 15 was used), respectively as a herbicide and as an adjuvant. Tables 6A and 6B show the results.

TABLE 6A

| Test No. | Content of Agricultural chemical (ppm) | Content of Adjuvant (ppm) | Agr. chemical/ Adjuvant (weight ratio) | Herbicidal rate (%) |
| --- | --- | --- | --- | --- |
| 1 | 2000 | 200 | 1/0.1 | 94.5 |
| 2 | 2000 | 1000 | 1/0.5 | 100.0 |
| 3 | 2000 | 2000 | 1/1.0 | 100.0 |
| 4 | 2000 | 10000 | 1/5 | 100.0 |
| 5 | 2000 | 24000 | 1/12 | 100.0 |
| 6 | 2000 | 30000 | 1/15 | 100.0 |
| 7 | 2000 | 80000 | 1/40 | 100.0 |
| 8 | 2000 | 0 | — | 30.4 |
| 9 | 0 | 0 | — | 0.0 |

TABLE 6B

| Test No. | Content of Agricultural chemical (ppm) | Content of Adjuvant (ppm) | Agr. chemical/ Adjuvant (weight ratio) | Herbicidal rate (%) |
| --- | --- | --- | --- | --- |
| 10 | 2000 | 200 | 1/0.1 | 85.4 |
| 11 | 2000 | 1000 | 1/0.5 | 95.5 |
| 12 | 2000 | 2000 | 1/1.0 | 100.0 |
| 13 | 2000 | 10000 | 1/5 | 100.0 |
| 14 | 2000 | 24000 | 1/12 | 100.0 |
| 15 | 2000 | 30000 | 1/15 | 100.0 |
| 16 | 2000 | 80000 | 1/40 | 100.0 |
| 17 | 2000 | 0 | — | 30.4 |
| 18 | 0 | 0 | — | 0.0 |

EXAMPLE 7

The test described in the above Example 3 was repeated except that Sumithion emulsion and the adjuvants 1 or 14 described in Example 1 were employed, each in the amount specified in Tables 7A (the adjuvant 1 was used) and 7B (the adjuvant 14 was used), respectively as an insecticide and as an adjuvant. Tables 7A and 7B show the results.

TABLE 7A

| Test No. | Content of Agricultural chemical (ppm) | Content of Adjuvant (ppm) | Agr. chemical/ Adjuvant (weight ratio) | Insecticidal rate (%) |
| --- | --- | --- | --- | --- |
| 1 | 250 | 25 | 1/0.1 | 63.5 |
| 2 | 250 | 125 | 1/0.5 | 74.2 |
| 3 | 250 | 250 | 1/1.0 | 78.6 |
| 4 | 250 | 500 | 1/2.0 | 81.3 |
| 5 | 250 | 1000 | 1/4.0 | 100.0 |

TABLE 7A-continued

| Test No. | Content of Agricultural chemical (ppm) | Content of Adjuvant (ppm) | Agr. chemical/ Adjuvant (weight ratio) | Insecticidal rate (%) |
| --- | --- | --- | --- | --- |
| 6 | 250 | 2500 | 1/10 | 100.0 |
| 7 | 250 | 5000 | 1/20 | 100.0 |
| 8 | 250 | 0 | — | 51.2 |
| 9 | 0 | 0 | — | 0.0 |

TABLE 7B

| Test No. | Content of Agricultural chemical (ppm) | Content of Adjuvant (ppm) | Agr. chemical/ Adjuvant (weight ratio) | Insecticidal rate (%) |
| --- | --- | --- | --- | --- |
| 10 | 250 | 25 | 1/0.1 | 73.3 |
| 11 | 250 | 125 | 1/0.5 | 86.7 |
| 12 | 250 | 250 | 1/1.0 | 93.3 |
| 13 | 250 | 500 | 1/2.0 | 96.7 |
| 14 | 250 | 1000 | 1/4.0 | 100.0 |
| 15 | 250 | 2500 | 1/10 | 100.0 |
| 16 | 250 | 5000 | 1/20 | 100.0 |
| 17 | 250 | 0 | — | 53.3 |
| 18 | 0 | 0 | — | 0.0 |

EXAMPLE 8

The test described in the above Example 2 was repeated except that Osadan wettable powder and the adjuvants 5 or 18 described in Example 1 were employed, each in the amount specified in Tables 8A (the adjuvant 5 was used) and 7B (the adjuvant 18 was used), respectively as a miticide and as an adjuvant. Tables 8A and 8B show the results.

TABLE 8A

| Test No. | Content of Agricultural chemical (ppm) | Content of Adjuvant (ppm) | Agr. chemical/ Adjuvant (weight ratio) | Miticidal rate (%) |
| --- | --- | --- | --- | --- |
| 1 | 100 | 10 | 1/0.1 | 89.2 |
| 2 | 100 | 50 | 1/0.5 | 94.2 |
| 3 | 100 | 100 | 1/1.0 | 98.6 |
| 4 | 100 | 200 | 1/2.0 | 100.0 |
| 5 | 100 | 1000 | 1/10 | 100.0 |
| 6 | 100 | 1500 | 1/15 | 100.0 |
| 7 | 100 | 2000 | 1/20 | 100.0 |
| 8 | 100 | 0 | — | 48.0 |
| 9 | 0 | 0 | — | 0.0 |

TABLE 8B

| Test No. | Content of Agricultural chemical (ppm) | Content of Adjuvant (ppm) | Agr. chemical/ Adjuvant (weight ratio) | Miticidal rate (%) |
| --- | --- | --- | --- | --- |
| 10 | 100 | 10 | 1/0.1 | 77.8 |
| 11 | 100 | 50 | 1/0.5 | 88.9 |
| 12 | 100 | 100 | 1/1.0 | 94.4 |
| 13 | 100 | 200 | 1/2.0 | 98.9 |
| 14 | 100 | 1000 | 1/10 | 98.9 |
| 15 | 100 | 1500 | 1/15 | 100.0 |
| 16 | 100 | 2000 | 1/20 | 100.0 |
| 17 | 100 | 0 | — | 44.4 |
| 18 | 0 | 0 | — | 0.0 |

EXAMPLE 9

The test described in the above Example 2 was repeated except that Osadan wettable powder and the adjuvants 7 or 20 described in Example i were employed, each in the amount specified in Tables 9A (the adjuvant 7 was used) and 9B (the adjuvant 20 was used), respectively as a miticide and as an adjuvant. Tables 9A and 9B show the results.

TABLE 9A

| Test No. | Content of Agricultural chemical (ppm) | Content of Adjuvant (ppm) | Agr. chemical/ Adjuvant (weight ratio) | Miticidal rate (%) |
| --- | --- | --- | --- | --- |
| 1 | 100 | 10 | 1/0.1 | 69.4 |
| 2 | 100 | 50 | 1/0.5 | 78.6 |
| 3 | 100 | 100 | 1/1.0 | 100.0 |
| 4 | 100 | 200 | 1/2.0 | 100.0 |
| 5 | 100 | 1000 | 1/10 | 100.0 |
| 6 | 100 | 1500 | 1/15 | 100.0 |
| 7 | 100 | 2000 | 1/20 | 100.0 |
| 8 | 100 | 0 | — | 48.0 |
| 9 | 0 | 0 | — | 0.0 |

TABLE 9B

| Test No. | Content of Agricultural chemical (ppm) | Content of Adjuvant (ppm) | Agr. chemical/ Adjuvant (weight ratio) | Miticidal rate (%) |
| --- | --- | --- | --- | --- |
| 10 | 100 | 10 | 1/0.1 | 66.7 |
| 11 | 100 | 50 | 1/0.5 | 88.9 |
| 12 | 100 | 100 | 1/1.0 | 100.0 |
| 13 | 100 | 200 | 1/2.0 | 98.9 |
| 14 | 100 | 1000 | 1/10 | 98.9 |
| 15 | 100 | 1500 | 1/15 | 100.0 |
| 16 | 100 | 2000 | 1/20 | 100.0 |
| 17 | 100 | 0 | — | 44.4 |
| 18 | 0 | 0 | — | 0.0 |

The invention being thus described, it will be obvious that the same may varied in many ways. Such variations are not to be regarded as a departure from the spirit and scope of the invention, and all such modifications as would be obvious to one skilled in the art are intended to be included within the scope of the following claims.

What we claimed is:

1. An agricultural chemical composition (1) comprising a mixture of compounds represented by the following general formula (I) and having (n1+n2+n3) and (n4+n5+n6) each being a number of 0 to 100 on the average and an agricultural chemical, wherein the weight ratio of the mixture to the agricultural chemical ranges from 0.1 to 50:

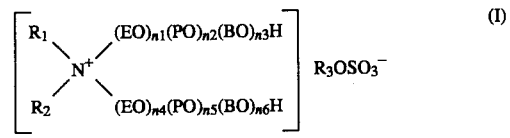

wherein $R_1$ and $R_2$ each represent a straight-chain or branched alkyl, alkenyl or hydroxyalkyl group having from 1 to 30 carbon atoms; $R_3$ represents a straight-chain or branched alkyl group having from 1 to 4 carbon atoms;

(EO)$_{n1}$ and (EO)$_{n4}$ each represent a polyoxyethylene chain;

(PO)$_{n2}$ and (PO)$_{n5}$ each represent a polyoxypropylene chain;

(BO)$_{n3}$ and (BO)$_{n6}$ each represent a polyoxybutylene chain;

n1, n2, n3, n4, n5 and n6 each are 0 or a positive integer; and (n1+n2+n3) and (n4+n5+n6) each are 0 or a positive integer provided that at least one of (n1+n2+n3) and (n4+n5+n6) is 1 or more.

2. The agricultural chemical composition (1) as claimed in claim 1, wherein $R_1$ is a straight-chain or branched alkyl, alkenyl or hydroxyalkyl group having from 8 to 24 carbon atoms and $R_2$ is a straight-chain or branched alkyl, alkenyl or hydroxyalkyl group having from 1 to 4 carbon atoms.

3. The agricultural chemical composition (1) as claimed in claim 1, wherein $R_1$ is a group selected from the group consisting of octyl, decyl, lauryl, myristyl, palmityl, stearyl and oleyl groups and $R_2$ and $R_3$ each are a group selected from the group consisting of methyl, ethyl, hydroxyethyl and hydroxypropyl groups.

4. The agricultural chemical composition (1) as claimed in claim 1, wherein the mixture is a quaternized N,N,N,N-lauryl ethyl di[(poly)oxyethylene] $(\overline{n1+n4=2})$ ammonium ethyl sulfate, a quaternized N,N,N,N-oleylmethyl di[(poly)oxyethylene] $(\overline{n1+n4=2})$ ammonium methylsulfate, a quaternized N,N,N,N-lauryl methyl di[(poly)oxyethylene] $(\overline{n1+n4=15})$ ammonium methylsulfate or a quaternized N,N,N,N-oleyl methyl di[(poly)oxypropylene] $(\overline{n2+n5=14})$ ammonium methylsulfate.

5. The agricultural chemical composition (1) as claimed in claim 1, wherein (n1+n2+n3) and (n4+n5+n6) of the mixture are each from 0 to 100.

6. The agricultural chemical composition (1) as claimed in claim 1, wherein (n1+n2+n3) and (n4+n5+n6) of the mixture are each from 0 to 50 and (n1+n2+n3+n4+n5+n6) is from 1 to 100.

7. The agricultural chemical composition (1) as claimed in claim 1, wherein (n1+n2+n3) and (n4+n5+n6) of the mixture are each from 1 to 25 and (n1+n2+n3+n4+n5+n6) is from 2 to 50.

8. The agricultural chemical composition (1) as claimed in claim 1, wherein the agricultural chemical is selected from the group consisting of active ingredients of bactericides, insecticides, miticides, herbicides and plant growth regulators.

9. The agricultural chemical composition according to claim 1, wherein said agricultural chemical is N-(phosphonomethyl) glycine isopropylamine salt.

10. An agricultural chemical composition (1) comprising a mixture of compounds represented by the following general formula (I) and having (n1+n2+n3) and (n4+n5+n6) each being a number of 1 to 100 on the average and an agricultural chemical, wherein the weight ratio of the mixture to the agricultural chemical ranges from 0.1 to 50:

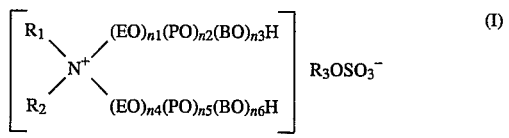

wherein $R_1$ and $R_2$ each represent a straight-chain or branched alkyl, alkenyl or hydroxyalkyl group having from 1 to 30 carbon atoms; $R_3$ represents a straight-chain or branched alkyl group having from 1 to 4 carbon atoms;

$(EO)_{n1}$ and $(EO)_{n4}$ each represent a polyoxyethylene chain;

$(PO)_{n2}$ and $(PO)_{n5}$ each represent a polyoxypropylene chain;

$(BO)_{n3}$ and $(BO)_{n6}$ each represent a polyoxybutylene chain;

n1, n2, n3, n4, n5 and n6 each are 0 or a positive integer; and (n1+n2+n3) and (n4+n5+n6) each are 1 or a positive integer.

11. The agricultural chemical composition according to claim 10, wherein said agricultural chemical is N-(phosphonomethyl) glycine isopropylamine salt.

12. An agricultural chemical composition (2) comprising a mixture of compounds represented by the following general formula (I) and having (n1+n2+n3) and (n4+n5+n6) each being a number of 0 to 100 on the average and a surfactant other than the compounds represented by the following general formula (I) as adjuvants and an agricultural chemical, wherein the weight ratio of the total amount of the adjuvants to the agricultural chemical ranges from 0.1 to 50:

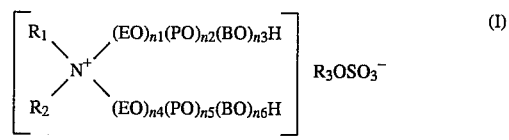

wherein $R_1$, $R_2$ and $R_3$ each represent a straight-chain or branched alkyl, alkenyl or hydroxyalkyl group having from 1 to 30 carbon atoms;

$(EO)_{n1}$ and $(EO)_{n4}$ each represent a polyoxyethylene chain;

$(PO)_{n2}$ and $(PO)_{n5}$ each represent a polyoxypropylene chain;

$(BO)_{n3}$ and $(BO)_{n6}$ each represent a polyoxybutylene chain;

n1, n2, n3, n4, n5 and n6 each are 0 or a positive integer; and (n1+n2+n3) and (n4+n5+n6) each are 0 or a positive integer provided that at least one of (n1+n2+n3) and (n4+n5+n6) is 1 or more.

13. The agricultural chemical composition (2) as claimed in claim 12, wherein $R_1$ is a straight-chain or branched alkyl, alkenyl or hydroxyalkyl group having from 8 to 24 carbon atoms and $R_2$ and $R_3$ each are a straight-chain or branched alkyl, alkenyl or hydroxyalkyl group having from 1 to 4 carbon atoms.

14. The agricultural chemical composition (2) as claimed in claim 12, wherein $R_1$ is a group selected from the group consisting of octyl, decyl, lauryl, myristyl, palmityl, stearyl and oleyl groups and $R_2$ and $R_3$ each are a group selected from the group consisting of methyl, ethyl, hydroxyethyl and hydroxypropyl groups.

15. The agricultural chemical composition (2) as claimed in claim 12, wherein the mixture is a quaternized N,N,N,N-lauryl ethyl di[(poly)oxyethylene] $(\overline{n1+n4=2})$ ammonium ethyl sulfate, a quaternized N,N,N,N-oleylmethyl di[(poly)oxyethylene] $(\overline{n1+n4=2})$ ammonium methylsulfate, a quaternized N,N,N,N-lauryl methyl di[(poly)oxyethylene] $(\overline{n1+n4=15})$ ammonium methylsulfate or a quaternized N,N,N,N-oleyl methyl di[(poly)oxypropylene] $(\overline{n2+n5=14})$ ammonium methylsulfate.

16. The agricultural chemical composition (2) as claimed in claim 12, wherein (n1+n2+n3) and (n4+n5+n6) of the mixture are each from 0 to 100.

17. The agricultural chemical composition (2) as claimed in claim 12, wherein (n1+n2+n3) and (n4+n5+n6) of the mixture are each from 0 to 50 and (n1+n2+n3+n4+n5+n6) is from 1 to 100.

18. The agricultural chemical composition (2) as claimed in claim 12, wherein (n1+n2+n3) and (n4+n5+n6) of the mixture are each from 1 to 25 and (n1+n2+n3+n4+n5+n6) is from 2 to 50.

19. The agricultural chemical composition (2) as claimed in claim 12, wherein the agricultural chemical is selected from the group consisting of active ingredients of bactericides, insecticides, miticides, herbicides and plant growth regulators.

20. The agricultural chemical composition (2) as claimed in claim 12, wherein the surfactant is a nonionic surfactant.

21. The agricultural chemical composition (2) as claimed in claim 12, wherein the weight ratio of the mixture of compounds represented by the general formula (I) to the surfactant other than the compounds represented by the general formula (I) ranges from 1:10 to 50:1.

22. The agricultural chemical composition (2) as claimed in claim 12, wherein the weight ratio of the mixture of compounds represented by the general formula (I) to the surfactant other than the compounds represented by the general formula (I) ranges from 1:1 to 10:1.

23. A bactericidal, insecticidal, miticidal, herbicidal or plant growth regulating method (1), comprising applying to the pest to be controlled or to the plant to be regulated an effective amount of an agricultural chemical composition (3) comprising from 0.02 to 8% by weight of a mixture of compounds represented by the following general formula (I) and having (n1+n2+n3) and (n4+n5+n6) each being a number of 0 to 100 on the average and an agricultural chemical which is present in an amount of from 0.02 to 10 times as much as the mixture:

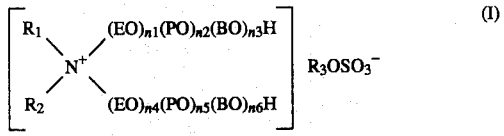

wherein $R_1$, $R_2$ and $R_3$ each represent a straight-chain or branched alkyl, alkenyl or hydroxyalkyl group having from 1 to 30 carbon atoms;

$(EO)_{n1}$ and $(EO)_{n4}$ each represent a polyoxyethylene chain;

$(PO)_{n2}$ and $(PO)_{n5}$ each represent a polyoxypropylene chain;

$(BO)_{n3}$ and $(BO)_{n6}$ each represent a polyoxybutylene chain;

n1, n2, n3, n4, n5 and n6 each are 0 or a positive integer; and (n1+n2+n3) and (n4+n5+n6) each are 0 or a positive integer provided that at least one of (n1+n2+n3) and (n4+n5+n6) is 1 or more.

24. A bactericidal, insecticidal, miticidal, herbicidal or plant growth regulating method (2), comprising applying to the pest to be controlled or to the plant to be regulated an effective amount of an agricultural chemical composition (4) comprising from 0.02 to 8% by weight of adjuvants comprising a mixture of compounds represented by the following general formula (I) and having (n1+n2+n3) and (n4+n5+n6) each being a number of 0 to 100 on the average and a surfactant other than the compounds represented by the following general formula (I), and an agricultural chemical which is present in an amount of from 0.02 to 10 times as much as the total amount of the adjuvants:

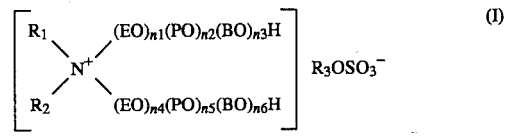

wherein $R_1$, $R_2$ and $R_3$ each represent a straight-chain or branched alkyl, alkenyl or hydroxyalkyl group having from 1 to 30 carbon atoms;

$(EO)_{n1}$ and $(EO)_{n4}$ each represent a polyoxyethylene chain;

$(PO)_{n2}$ and $(PO)_{n5}$ each represent a polyoxypropylene chain;

$(BO)_{n3}$ and $(BO)_{n6}$ each represent a polyoxybutylene chain;

n1, n2, n3, n4, n5 and n6 each are 0 or a positive integer; and (n1+n2+n3) and (n4+n5+n6) each are 0 or a positive integer provided that at least one of (n1+n2+n3) and (n4+n5+n6) is 1 or more.

* * * * *